United States Patent [19]

Kettler

[11] Patent Number: 5,031,099
[45] Date of Patent: Jul. 9, 1991

[54] PROCESS FOR THE EVALUATION OF CELL PICTURES

[75] Inventor: Albrecht Kettler, Aalen, Fed. Rep. of Germany

[73] Assignee: Carl-Zeiss-Stiftung, Heidenheim/Brenz, Fed. Rep. of Germany

[21] Appl. No.: 428,217

[22] Filed: Oct. 27, 1989

Related U.S. Application Data

[63] Continuation-in-part of Ser. No. 198,294, May 25, 1988, Pat. No. 4,907,158.

[30] Foreign Application Priority Data

Oct. 28, 1988 [DE] Fed. Rep. of Germany ....... 3836716

[51] Int. Cl.$^5$ ............................................. G06F 15/42
[52] U.S. Cl. ........................... 364/413.08; 364/413.01
[58] Field of Search ...................... 364/413.01, 413.08; 382/6, 36; 377/6, 10; 358/105

[56] References Cited

U.S. PATENT DOCUMENTS

| | | | |
|---|---|---|---|
| 4,320,415 | 3/1982 | Jones | 358/105 |
| 4,513,438 | 4/1985 | Graham et al. | 382/6 |
| 4,700,298 | 10/1987 | Palcic et al. | 364/413.01 |
| 4,724,543 | 2/1988 | Klevecz et al. | 382/6 |
| 4,907,158 | 3/1990 | Kettler et al. | 364/413.01 |

OTHER PUBLICATIONS

"Computer-Assisted Analyses of Cell Locomotion and Chemotaxis," by P. B. Noble and M. D. Levine, published by CRC Press, Inc., Boca Raton, Florida, pp. 1, 2 and 49-76.

Primary Examiner—Jerry Smith
Assistant Examiner—David Huntley
Attorney, Agent, or Firm—Eugene Stephens & Associates

[57] ABSTRACT

A process and apparatus for evaluating pictures of cell cultures uses a computer-aided, observer-interactive system which records and reviews a chronological series of video pictures. The pictures are taken sequentially in each of a plurality of cell culture picture fields which border each other, each such field encompassing a different area of the specimen. Each successive chronological picture is displayed on a monitor where it is reviewed by an observer who uses a digitizing pad to apply distinguishing marks to individual cells and/or cell groups. Picture-memory-an-analysis software is used to facilitate the marking process so that observer work effort and time are remarkably reduced. Stored information relating to the position and number of the distinguishing marks applied to each chronological picture is used to generate statistical graphs and data concerning the division rate of individual cell groups, the mobility of cells, cell pedigrees, and similar matters.

9 Claims, 7 Drawing Sheets

PROCESS FOR THE EVALUATION OF CELL PICTURES

RELATED APPLICATIONS

This is a continuation-in-part of commonly owned application Ser. No. 07/198,294, filed 25 May 1988, and issued as U.S. Pat. No. 4,907,158, on 6 Mar. 1990.

BACKGROUND

In recent years, the evaluation of pictures of cell cultures has been assuming ever greater significance not only in research but in routine examinations as well. In addition to exploring the cell growth of primary cultures (e.g., tumors), special attention is being given to examining the influence of outside effects on the growth and mobility of cell structures in such procedures as toxicity and mutagenicity tests, determining the compatibility of implant materials, and monitoring the effects of pharmaceuticals. Emphasis is also being placed upon the examination of cell cultures in preference to, or in order to dispense with, making toxicity tests on higher organisms, i.e., test animals.

In order to provide statistically relevant information for the various procedures referred to above, it is necessary to examine a large number of cells. In many cases, e.g., for mutagenicity examinations, it is important to analyze the mobility performance of cell groups and to even determine the exact "fate" of individual cells.

Since such cell cultures involve large numbers of cells, the visual observation of the movement and/or structural transformation of individual cells is an extremely difficult and time-consuming task.

Therefore, for many routine cell culture evaluation procedures, for instance where counts must be made of the total number of cells in a specific field, assistance is being provided by computers. In some instances, where there is no requirement for highly accurate evaluations, computers are even being employed for fully automatic picture analysis. However, known computer systems are unsuited for more demanding procedures such as the analysis of cell mobility or the determination of cell pedigrees (genealogical tables). For these more demanding procedures, interactive, computer-aided systems are better suited.

A summary of possible interactive and automated processes for analyzing the mobility of cell cultures is described in the book, *Computer Assisted Analyses of Cell Locomotion and Chemotaxis*, by P. B. Noble and M. D. Devine, published by CRC Press, Inc., Boca Raton, Florida.

The interactive computer processes described in that reference relate only to cell locomotion, with the evaluations being limited to a relatively few selected cells. Therefore, the computer-aided processes disclosed in that reference do not solve the needs to which the subject invention is directed, namely, gathering developmental history of cells in regard to such matters as cell division rate and/or the number of different generation sequences of a number of cells, such histories being large enough to be statistically significant.

SUMMARY OF THE INVENTION

The subject invention provides a computer-aided, observer-interactive system which records, in parallel fashion, a chronological series of video pictures taken sequentially in each of a plurality of cell culture picture fields which border each other, each such field encompassing a different area of the specimen culture. Each successive chronological picture is displayed on a monitor where it is reviewed and marked by an observer, and the data gathered during this review and marking procedure is stored, providing a record from each picture in the chronological series taken for each of the respective picture fields. This data is recorded in sufficiently large numbers to permit statistically meaningful evaluation.

In any single picture, there are usually several groups or lines of cells to be monitored. According to the invention, computer assisted means are used, first, to mark each individual cell or group with respective distinguishing marks and, thereafter, to carry these identifying marks forward into the next successive chronological picture. In this manner, only the first picture in any chronological series need be fully marked by the observer, and in each of the following pictures these original markings only need to be updated to reflect changes occurring due to such things as cell shifts, cell division or cytolysis, and the migration or emigration of individual cells from the particular picture field. This computer-aided, interactive procedure provides a remarkable reduction in both observer work effort and time.

Further, the invention provides a digital record of each cell culture picture including the time it was taken, the relative position and number of individual cells and cell groups, as well as specifically identifying each separate generation of cell division. This data is especially informative in that it is possible to produce evaluations which eliminate the adulterating influence of dead cells or cells that have migrated into the picture field or emigrated from it.

This recorded data can be used to determine valuable statistics related to such matters as the division rate for individual groups of cells, the mobility of various cells, and even the maximum number of generational sequences until the cell culture decays. Also, such statistical information can be organized into appropriate tables and charts, e.g., a cell pedigree for individual cells, and this information can be displayed on the system's video monitor.

As indicated above, the invention uses computer-generated marking of sequential pictures for automatically carrying forward the markings applied to individual cells in the previous picture. This important computer activity is facilitated by known picture-memory-and-analysis software which, in effect, superimposes each sequential picture over the previously displayed picture, comparing the pixels in each line of video information for each picture and adjusting the displayed position of the succeeding picture to minimize the effects of equipment shifts. However, it has been found that a skilled evaluator, working interactively with the computer to manually adjust the superimposed images, often obtains better discrimination between actual cell movements and inadvertent, random equipment shifts. In any event, by adapting this known software to the inventive process disclosed herein, it is possible to automatically or interactively minimize the effects of inadvertent movement of a specimen container and/or joint movement of the entire cell culture and, thus, to maximize the coincidence of automatically repeated markings with the same cells.

DETAILED DESCRIPTION

Figure 1:
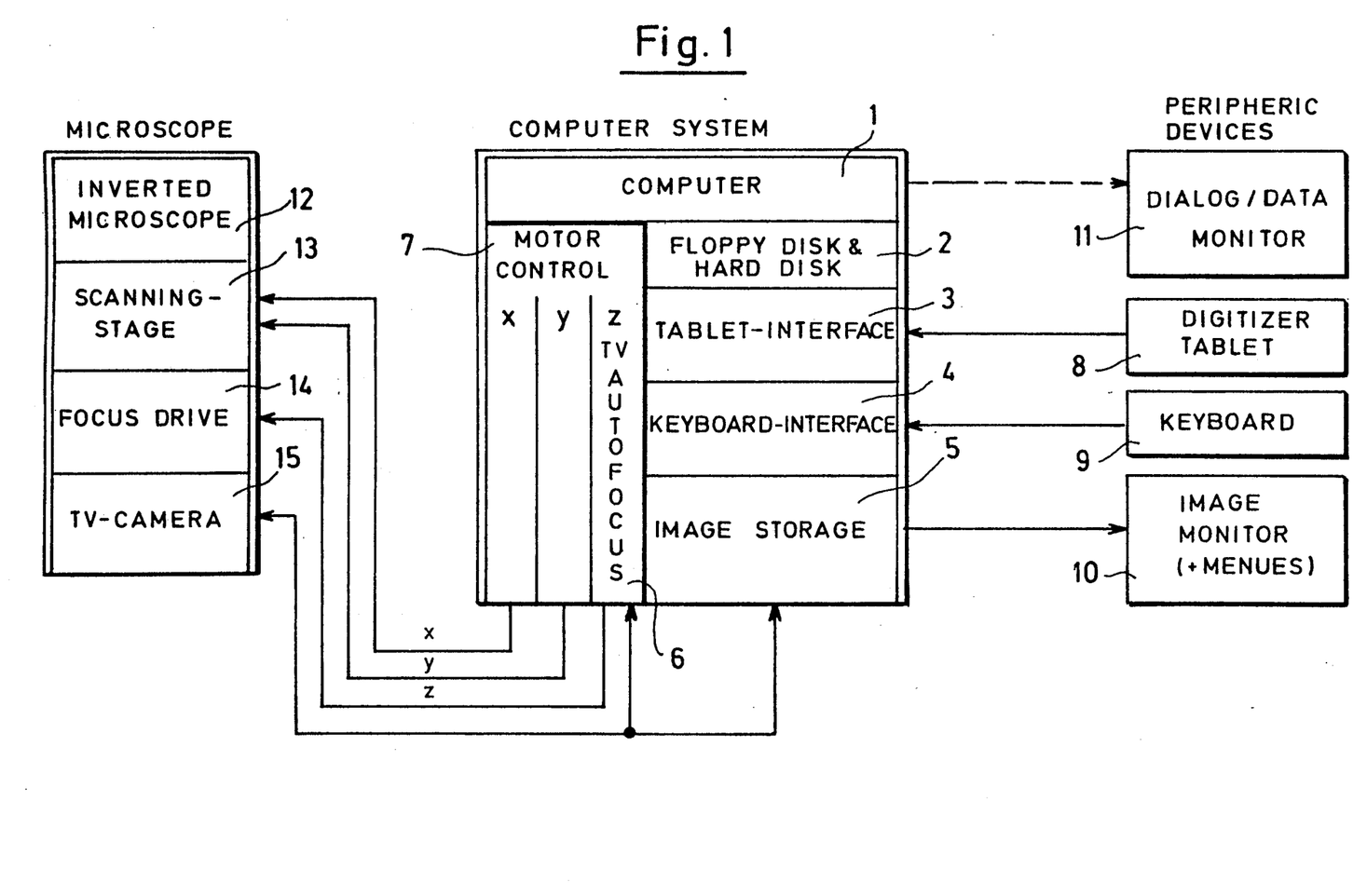
FIG. 1 is a block diagram of the components of a work station according to the invention.

As shown in FIG. 1, the work station according to the invention comprises three groups of components: a microscope, a computer system connected to the microscope, and peripheral devices enabling the observer to interact with the system.

The microscope (12) is a conventional inverted microscope having a specimen table or scanning-stage (13) movable in two coordinates. Microscope (12) is equipped with a powered focus drive (14) and includes an appropriately positioned television camera (15). Scanning-stage (13) positions the cell cultures being examined above the lens of the microscope, and it has an extra large range so that a number of specimen containers can be installed simultaneously and processed successively. Microscope apparatus similar to that just described is marketed by the Carl Zeiss company under the trademark "AXIOVERT".

Computer (1) may be any type of personal computer (e.g., an IBM PC/AT) which includes: (a) a memory (2) in the form of a floppy disk drive and a fixed disk drive, (b) a tablet interface (3) for connection of the digitizing tablet (8), and (c) a keyboard interface (4) to which the input keyboard (9) is connected.

Computer (1) is also equipped with a picture memory, i.e., image storage (5) which comprises known hardware and software modules for digitizing and processing the pictures recorded by camera (15). Suitable for such a picture memory are the modules offered by Matrox Electronic Systems Ltd. (a Canadian company located in Dorval, Quebec) under the designation "MVP-AT". Connected to image storage (5) is a monitor (10) on which cell pictures can be displayed and on which graphics generated for user dialogue can be superimposed. However, as indicated by the dashed arrow, such graphics may be displayed instead on a separate data dialogue monitor (11) which, for instance, may be the video screen of computer (1) that is available anyhow.

Integrated in computer (1) is a motor control (7) for energizing the drive motors which position the microscope's scanning-stage (13) and focus drive (14). Motor scanning-stage (13) and focus drive (14). Motor control (7) includes an autofocus system (6) which is responsive to the output of camera (15) and produces a focusing signal (Z) for moving focus drive (14) in the direction of maximum image contrast.

Operation of the above-described apparatus is as follows: Cell cultures contained in a plurality of specimen containers are appropriately positioned on the microscope's scanning stage (13) and monitored at regular intervals, e.g., every twenty minutes, or every two hours, etc. Such monitoring is accomplished by programming computer (1) so that, at each such interval, scanning stage (13) and TV camera (15) are activated to record a series of video pictures of a plurality of successive picture fields, each bordering at least one other such successive field and each encompassing a different area of one of the cell cultures being evaluated. Before each picture is taken, the microscope is automatically focused for maximum image contrast. This process is repeated for each of the specimen containers being monitored. The digitized pictures are transmitted to image memory (5), separated according to picture field, identified as to time taken, and stored on disks (2).

When monitoring is complete and all images have been recorded, the images for each individual picture field are sequentially retrieved from disks (2) in chronological order, and the sequential pictures are evaluated interactively. The evaluator views each picture, singly and successively, on monitor (10) and uses a cursor, controlled with the aid of digitizing pad (8), to mark the cells appearing on the monitor. This interactive evaluation process will now be described in more detail with reference to FIGS. 2–7 which are intended to illustrate a chronological series of sequential images taken of one picture field selected from a culture being examined.

The first image of the sequence (FIG. 2) shows the individual cells marked with the aid of appropriate software which enables the user to apply different marks for each of the various groups of cells (20, 21, 22, and 23).

Figure 2:
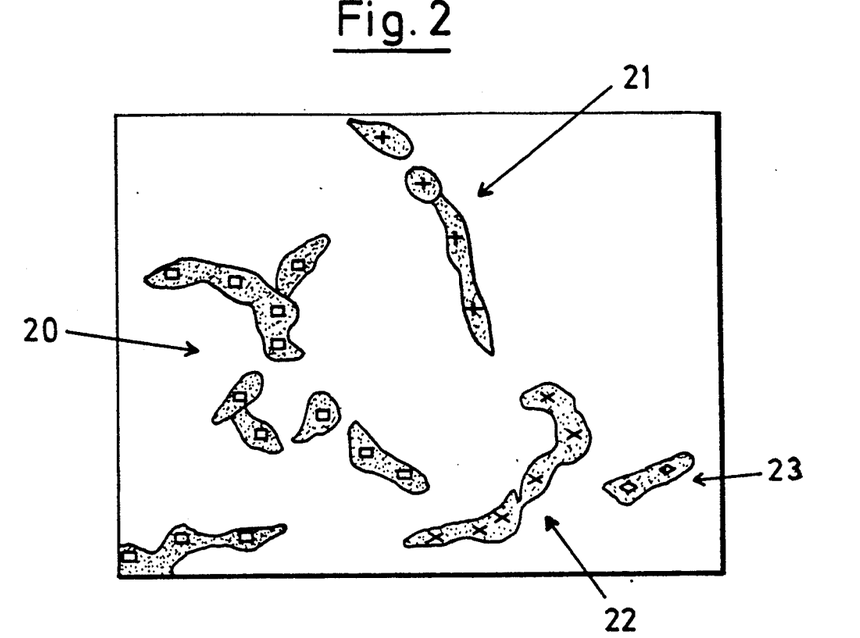
FIGS. 2 through 7 are sketches of a chronological series of cell culture pictures, showing individual cells and cell groups marked according to the invention.
Figure 3:
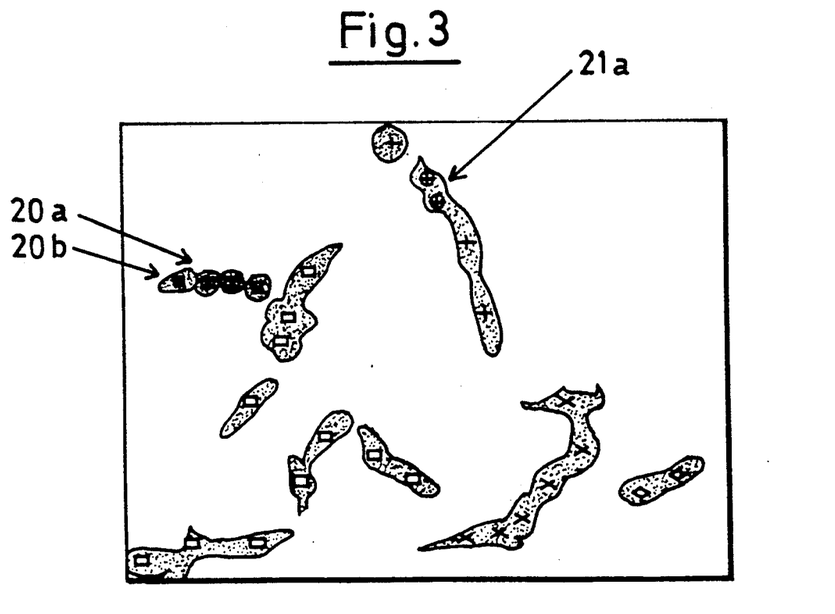
Figure 4:
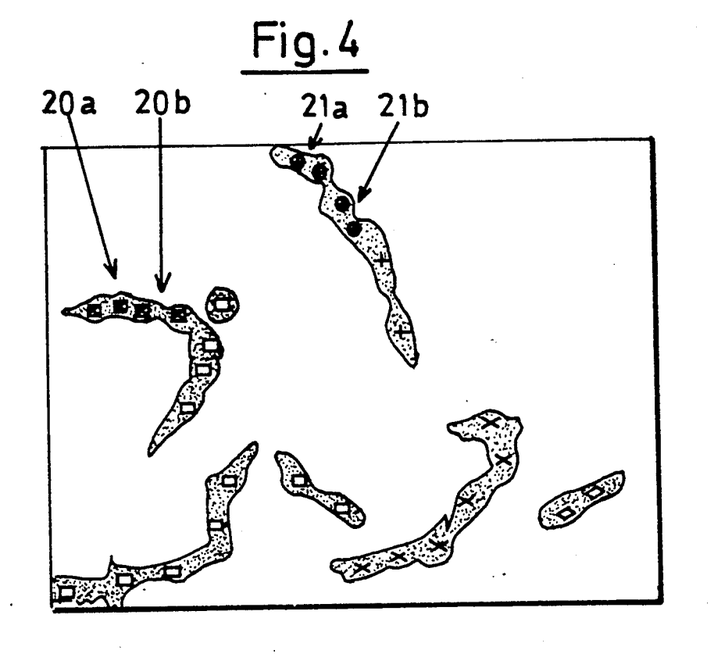
Figure 5:
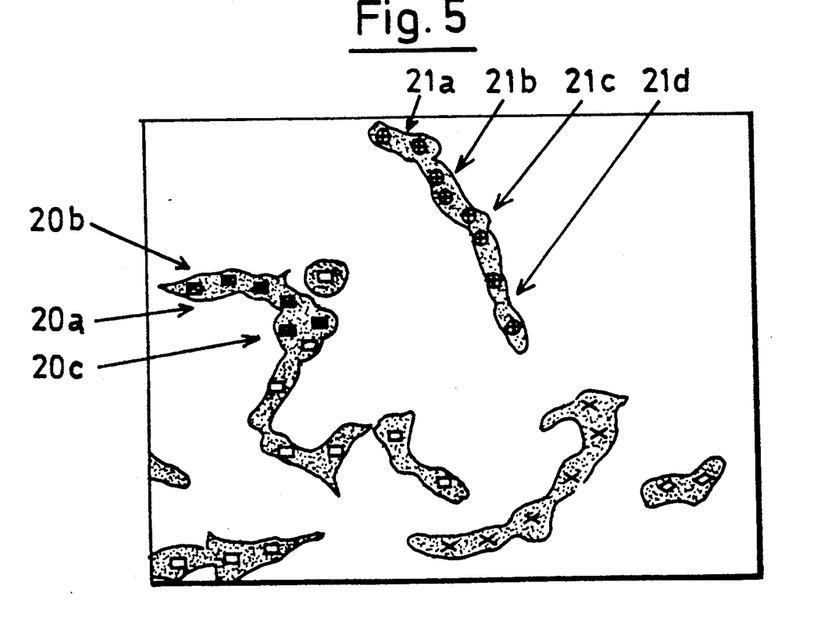
Figure 6:
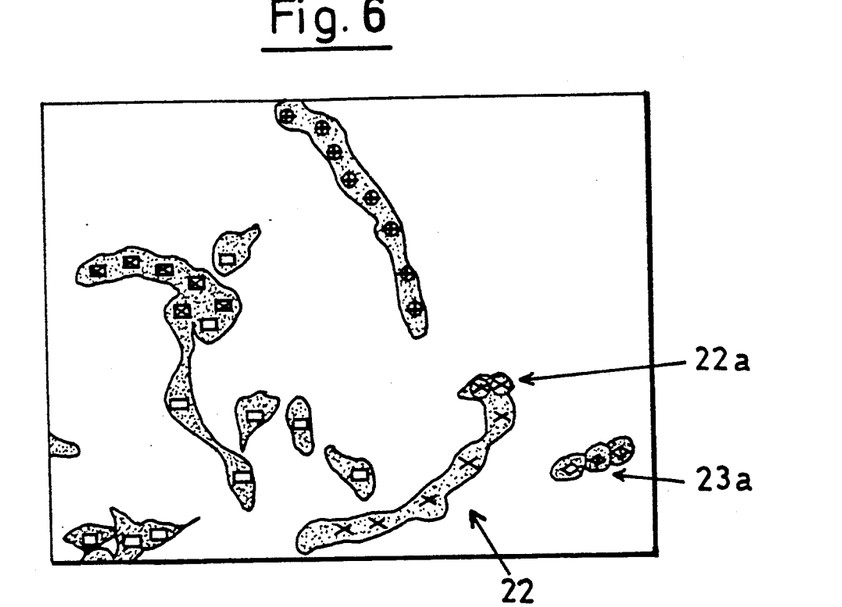
Figure 7:
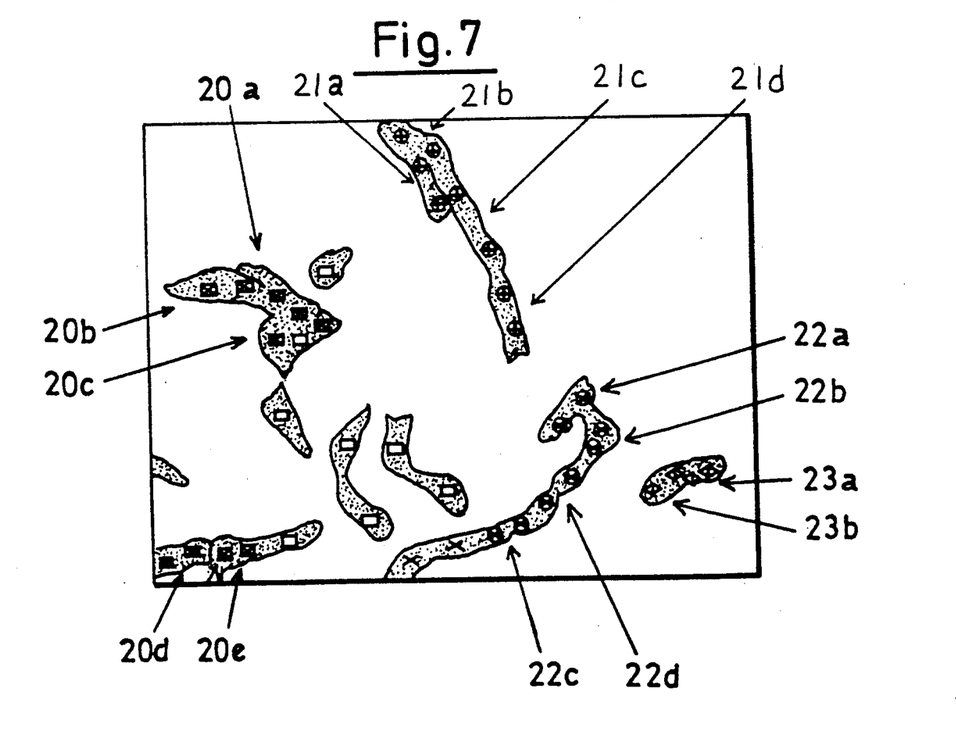

The next image of the sequence, illustrated in FIG. 3, is first positionally adjusted relative to the previous image (FIG. 2) by known software such as that identified earlier. Namely, computer (1) performs a real-time subtraction of the signals pertaining to specific pixels of both pictures, and it corrects any apparent shift of the crucial points of the cells that may have been caused by accidental movements of the entire picture field or by equipment drift. The cell marks that were already applied in FIG. 2 are automatically adopted in the new image (FIG. 3). Thus, the user only needs to correct for the changes that occur, such as, movements of individual cells, cell division and cell decay, as well as the emigration and migration of cells from and into the picture field.

For example, when the image of FIG. 3 is compared with that of FIG. 2, it is noted that divisions have occurred at two points (20a and 20b) in cell group (20), and at one point (21a) in cell group (21). These daughter cells are given special and different identifying marks. In the illustration of FIG. 3, the evaluator has chosen a double symbol for better visibility, namely, a square with a diagonal cross for the first generation daughter cells of cell group (20), and a circled cross for the daughter cells of group (21).

Further cell divisions are similarly noted by the evaluator in each of the chronological sequence of images shown in FIGS. 4–7, the daughter cells being identified with appropriate marks. By the elapsed time monitored by the image in FIG. 7, five cells of cell group (20) (see arrows 20a–20e), four cells of cell group (21) (arrows 21a–21d), four cells of cell group (22) (22a–22d) and two cells of cell group (23) (23a and 23b) have divided, and the daughter cells of the first generation have nearly doubled the number of cells in this particular image field.

Normally, these daughter cells will also divide again several times, and the evaluator will assign further identifying marks for each successive generation. However, this continuing process is not illustrated with additional figures.

Since the operator is only required to enter new marks for the changes appearing in each successive image, the just-described interactive procedure provides a remarkable saving of time and effort in the evaluation of cell pictures. Further, with some cultures it is possible to use the image memory software to further automate this procedure. During the comparison of each successive image with its predecessor, the computer can often recognize cell divisions and migrations, and it can apply the appropriate new markings. In such cases, the human evaluator merely reviews and corrects this automatic image analysis.

Computer (1) stores the number and position of each identifying mark for each of the chronological images of each picture field. This stored information is then used to derive pertinent statistical analyses relating to the monitored cell culture.

Figure 8:
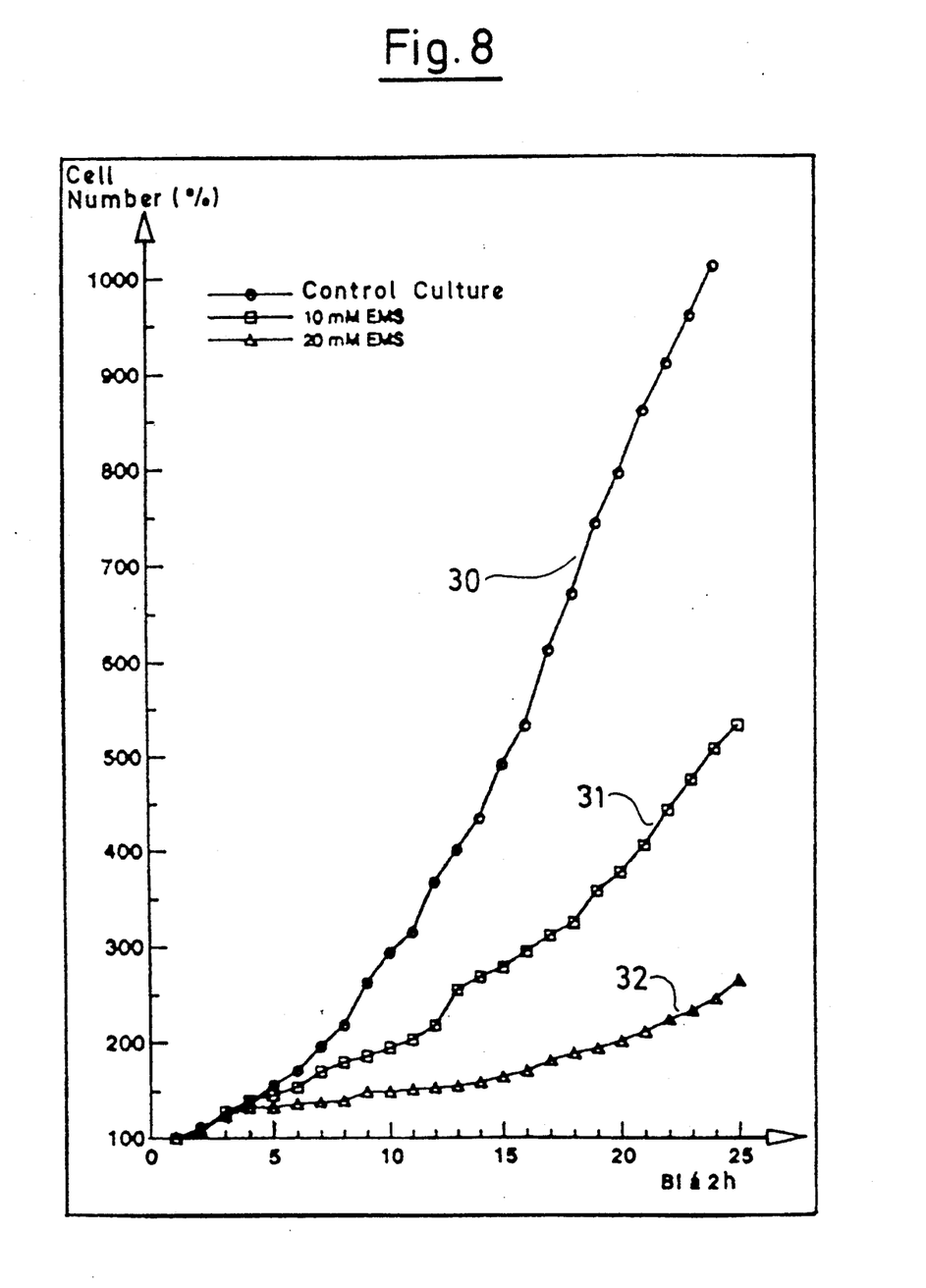
FIG. 8 is an exemplary graphic display relating to cell growth in three different cell cultures.

One such analysis, illustrated in FIG. 8, is based upon nothing more than a simple cumulative counting of the total number of cells noted during the entire monitoring of a particular cell culture. The curves (30, 31, and 32) show the cell growth, i.e., the absolute number of cells noted in all picture fields of each of three different cell cultures in successive monitoring periods. In FIG. 8, cell cultures represented by curves (31 and 32) had been exposed to concentrations of a toxic substance, while curve (30) indicates the growth of a control culture which was untreated.

Figure 9A:
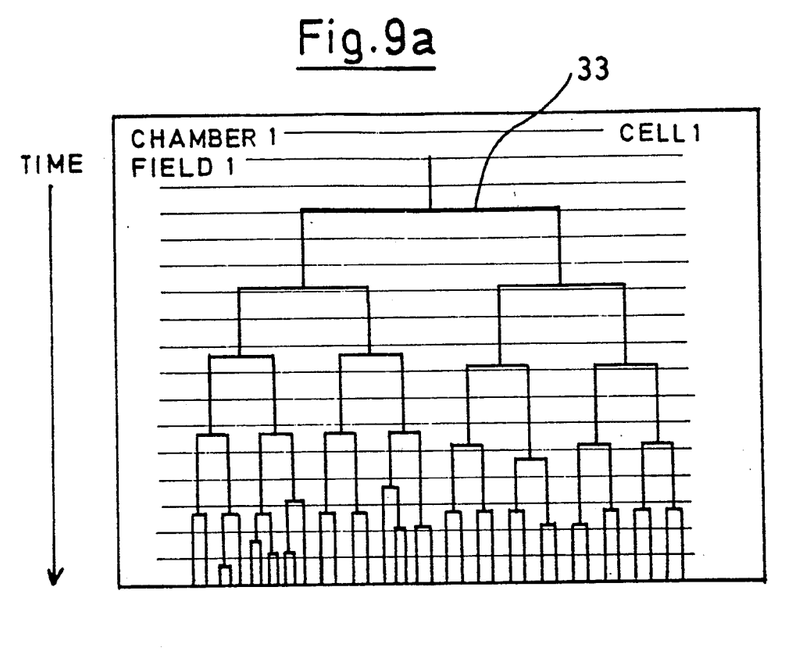
FIGS. 9a and 9b illustrate exemplary graphic displays of pedigrees for two different cells.
Figure 9B:
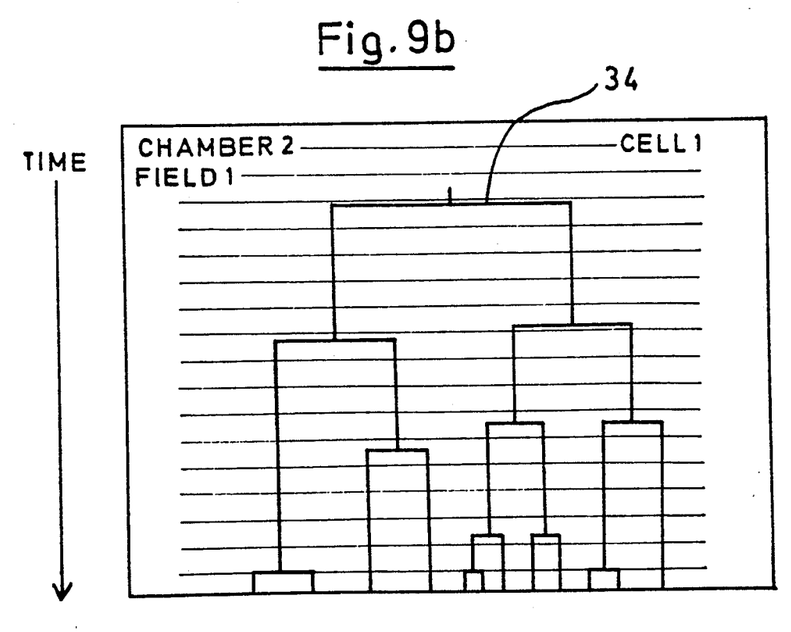

However, it will be appreciated that the information gathered and stored in the manner described above can be used to provide more complex analyses than total cell growth. The same stored information which was used to generate the curves shown in FIG. 8 also differentiates the generational changes occurring between sampled time periods. Thus, this same information can be used also to develop cell "pedigrees" (see FIGS. 9a and 9b) for any cell of the original population of each of the monitored cultures. FIG. 9a shows the pedigree (33) of one cell of the control culture. The horizontal lines superimposed over pedigree (33) represent constant intervals of time. Therefore, pedigree (33) indicates that the time cycle between successive generations of one of the original control cells is fairly constant and can be readily estimated. On the other hand, FIG. 9b illustrates a pedigree 34) of an original cell in one of the treated cultures. From pedigree (34), when compared to pedigree (33) in FIG. 9a, it can be seen that exposure to the toxic substance has resulted in less cell division and that the cycle time between successive individual generations is longer and less consistent.

Figure 10A:
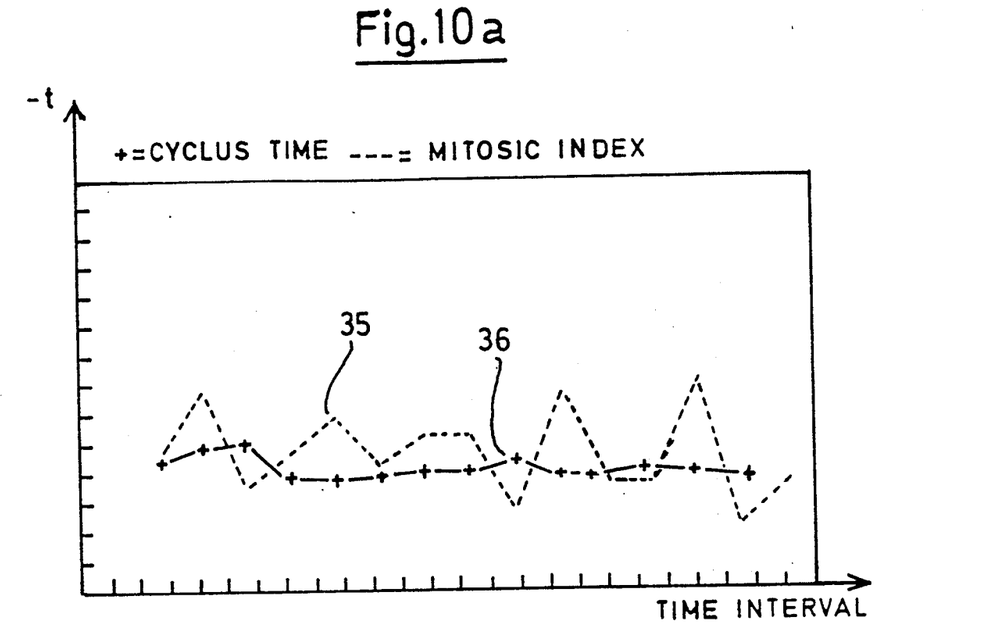
FIGS. 10a and 10b are diagrams comparing the time cycle and the mitosis index for the cells whose pedigrees are shown, respectively, in FIGS. 9a and 9b.
Figure 10B:
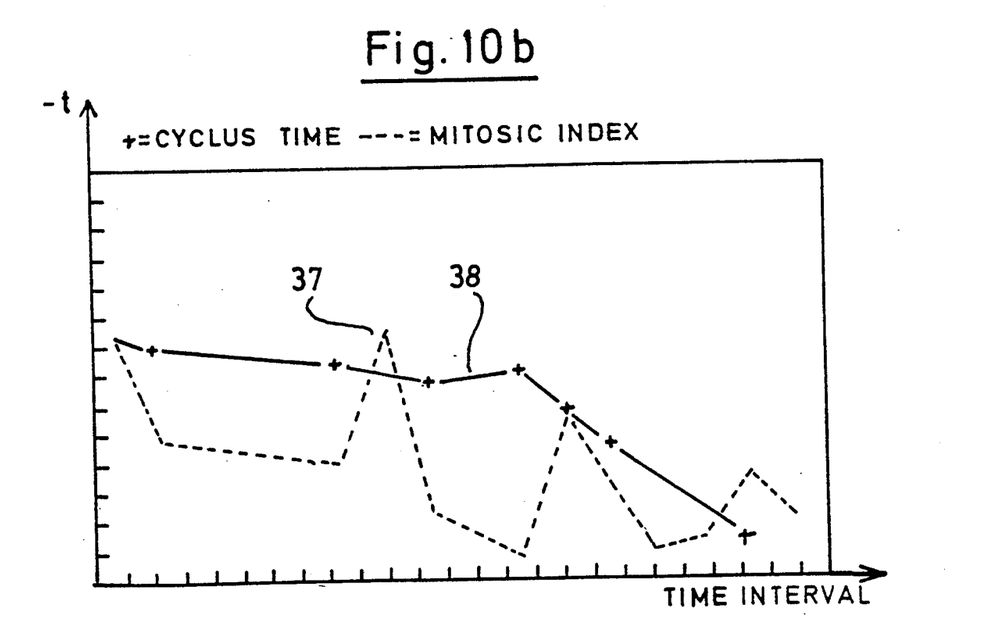

FIGS. 10a and 10b illustrate further statistical data which computer (1) can generate from the same stored information used to prepare the charts in FIGS. 9a and 9b. The graph in FIG. 10a shows the average values for the generational cycle time (36) and mitosis index (35) of all cells of the control population at each of the successively monitored time intervals. (The mitosis index is the division rate of a cell culture standardized to the total number of cells present in the culture during the time period being monitored.)

For cell populations growing undisturbed, cycle time and mitosis index remain generally constant, and this is reflected in the curves in FIG. 10a. In contrast, the curves shown in FIG. 10b relate to one of the cell populations to which a toxic substance had been added. The cycle times (38) are at first much higher, and then they become shorter as the cells recuperate. The mitosis index (37) appears, on average, to be lower for these treated cells.

Since this novel procedure provides chronological data identifying individual cell movement and replication, it will be appreciated that there are other statistical analyses and graphic representations that can be generated from the cell culture information that is sequentially recorded and interactively evaluated in the manner disclosed above. Further, as explained earlier, the interactive cell-marking procedure of the invention remarkably reduces the time and effort required to gather this information.

I claim:

1. A computer-aided, observer-interactive process for evaluating cell culture pictures in which several pictures of the same culture are taken chronologically and stored in digital form, comprising the steps of:
    successively recording and storing digitally pictures of a field encompassing at least a portion of the culture and having a size selected so that several individual cells will be located therein;
    sequentially displaying the digital pictures, in chronological order, on a video screen;
    marking the various individual cells in the first digital picture, each of the various cells or cell groups being provided different respective identifying marks;
    automatically marking the various individual cells with said different respective identifying marks in at least a second picture by computer means;
    interactively reviewing said automatically-provided identifying marks in sequentially displayed pictures by the observer for correcting any erroneously positioned marks; and
    storing digitally the position and number of each of the respective identifying marks in each sequential digital picture.

2. The process of claim 1 wherein, during said display step, each sequentially displayed digital picture is compared with the just previously displayed picture and positionally adjusted for equipment drift.

3. The process of claim 1 wherein each sequentially displayed digital picture adopts the respective markings of the just previously displayed picture and, during each said interactive reviewing step, the observer identifies cell variations by shifting such respective markings or by the addition of new identifying marks.

4. The process of claim 1 wherein the interactive reviewing step includes providing successive generations of cells with respective distinguishing marks, said process comprising the further step of determining and storing the number of marked cells in each successive generation.

5. The process of claim 1 comprising the further step of determining and storing the cell division rate for each differently marked cell or group of cells.

6. The process of claim 1 comprising the further step of determining and storing the mobility of each differently marked cell or group of cells.

7. The process of claim 1 comprising the further step of forming and displaying a pedigree chart on a video screen for each differently marked cell or group of cells.

8. The process of claim 1 wherein said process is repeated for a plurality of successive picture fields, each bordering at least one other such successive field and each encompassing a different area of the same cell culture being evaluated.

9. Apparatus for taking and evaluating cell culture pictures in which several pictures of the same culture are taken chronologically, stored in digital form, and then sequentially displayed for review by an observer, comprising:
- a microscope having a stage for holding a cell culture specimen to be examined, said staging positionable in at least two directions;
- television means for recording video pictures of the specimen;
- picture memory means for digitally storing said video pictures;
- a monitor for displaying said stored video pictures;
- electronic marking means, operable by said observer, for inserting a plurality of different identifying marks onto pictures displayed on the monitor;
- computer means for positioning said stage, for actuating said memory means to store said video pictures chronologically, for sequentially displaying said chronologically stored pictures on the monitor, and for storing the number and position of each identifying mark inserted on each sequentially displayed picture; and
- programming means for evaluating said stored information relating to the number and position of the identifying marks;
- said computer means including means for displaying, for each said sequentially displayed picture, the respective identifying marks as inserted or repositioned by said observer-operated electronic marking means.

* * * * *

Disclaimer

5,031,099—*Albrecht Kettler*, Aalen, Fed. Rep. of Germany. PROCESS FOR THE EVALUATION OF CELL PICTURES. Patent dated July 9, 1991. Disclaimer filed May 6, 1991, by the assignee, Carl-Zeiss-Stiftung.

The term of this patent subsequent to March 6, 2007 has been disclaimed.

[ *Official Gazette October 8, 1991* ]